United States Patent
Armoundas

(10) Patent No.: US 11,771,330 B2
(45) Date of Patent: Oct. 3, 2023

(54) SYSTEM AND METHOD FOR PROCESSING CARDIAC SIGNALS AND PROVIDING REPORTS TO USERS REGARDING IMPENDING OR ONGOING MEDICAL CONDITIONS

(71) Applicant: The General Hospital Corporation, Boston, MA (US)

(72) Inventor: Antonis A. Armoundas, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 343 days.

(21) Appl. No.: 16/957,162

(22) PCT Filed: Jan. 10, 2019

(86) PCT No.: PCT/US2019/013023
§ 371 (c)(1),
(2) Date: Jun. 23, 2020

(87) PCT Pub. No.: WO2019/140072
PCT Pub. Date: Jul. 18, 2019

(65) Prior Publication Data
US 2020/0329978 A1  Oct. 22, 2020

Related U.S. Application Data

(60) Provisional application No. 62/615,607, filed on Jan. 10, 2018.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0006* (2013.01); *A61B 5/0022* (2013.01);
(Continued)

(58) Field of Classification Search
CPC ... A61B 5/0205; A61B 5/0006; A61B 5/0022; A61B 5/352; A61B 5/363; A61B 5/366;
(Continued)

(56) References Cited

U.S. PATENT DOCUMENTS 7,025,729 B2   4/2006  de Chazal
8,265,752 B2   9/2012  Armoundas
(Continued)

OTHER PUBLICATIONS

Sayadi, O. et al. (2014). An optimized method for estimating the tidal volume from intracardiac or body surface electrocardiographic signals: implications for estimating minute ventilation. American Journal of Physiology—Heart and Circulatory Physiology, 307(3), H426-H436. (Year: 2014).*
(Continued)

*Primary Examiner* — Paula J Stice
(74) *Attorney, Agent, or Firm* — Burns & Levinson LLP; Steven M. Mills

(57) ABSTRACT

A system and a method are provided for using a mobile computing system comprising that has a communication connection configured to communicate with an electrocardiographic (ECG) apparatus to acquire ECG signals from the subject through a plurality of ECG leads. The system includes a processor configured to receive the ECG signals through the communications connection and process the ECG signals to estimate at least one of a respiratory rate of the subject, a tidal volume of the subject, or an ischemic index or repolarization alternans of the subject, from the ECG signals. The processor is further configured to generate an alert upon determining at least one of the ischemic index or repolarization alternans is above a threshold value or a
(Continued)

change in respiratory rate or tidal volume indicative of an abnormal respiratory event. The system also includes a display configured to display the alert.

15 Claims, 8 Drawing Sheets

(51) Int. Cl.
    *A61B 5/352*     (2021.01)
    *A61B 5/363*     (2021.01)
    *A61B 5/366*     (2021.01)

(52) U.S. Cl.
    CPC .............. *A61B 5/352* (2021.01); *A61B 5/363* (2021.01); *A61B 5/366* (2021.01); *A61B 5/7257* (2013.01); *A61B 5/742* (2013.01); *A61B 5/746* (2013.01)

(58) Field of Classification Search
    CPC ....... A61B 5/7257; A61B 5/742; A61B 5/746; A61B 5/349; A61B 5/364; A61B 5/316; A61B 5/7278
    See application file for complete search history.

(56) References Cited

U.S. PATENT DOCUMENTS

| | | | |
|---|---|---|---|
| 9,949,659 B2 | 4/2018 | Armoundas | |
| 2006/0041201 A1 | 2/2006 | Behbehani | |
| 2009/0326595 A1 | 12/2009 | Brockway | |
| 2012/0316611 A1* | 12/2012 | Armoundas | ....... A61N 1/39622 607/7 |
| 2013/0204100 A1 | 8/2013 | Acquista | |
| 2015/0272464 A1* | 10/2015 | Armoundas | ........... A61B 5/026 600/509 |
| 2016/0135706 A1 | 5/2016 | Sullivan et al. | |
| 2016/0331273 A1* | 11/2016 | Armoundas | ........... A61B 5/282 |

OTHER PUBLICATIONS

Adams KF, Jr., et al. Characteristics and outcomes of patients hospitalized for heart failure in the united states: Rationale, design, and preliminary observations from the first 100,000 cases in the acute decompensated heart failure national registry (adhere). Am Heart J. 2005; 149:209-216.
Adamson PB, et al. Ongoing right ventricular hemodynamics in heart failure: Clinical value of measurements derived from an implantable monitoring system. J Am Coll Cardiol. 2003;41:565-571.
Agarwal R, et al. Role of home blood pressure monitoring in overcoming therapeutic ninertia and improving hypertension control: A systematic review and meta-analysis. Hypertension. 2011;57:29-38.
Armoundas AA, et al. A novel pacing method to suppress repolarization alternans in vivo: Implications for arrhythmia prevention. Heart Rhythm. 2013;10:564-572.
Augousti AT, et al. Evaluation of cardiac monitoring using fiber optic plethysmography. Ann Biomed Eng. 2006,34:416-425.
Bonavia M, et al. Feasibility and validation of telespirometry in general practice: The italian "alliance" study. Respir Med. 2009; 103:1732-1737.
Chon KH, et al. Estimation of respiratory rate from photoplethysmogram data using time-frequency spectral estimation. IEEE Trans Biomed Eng. 2009;56:2054-2063.
Cohen KP, et al. Comparison of impedance and inductance ventilation sensors on adults during breathing, motion, and simulated airway obstruction. IEEE Trans Biomed Eng. 1997;44:555-566.
De Luca G, et al. Time delay to treatment and mortality in primary angioplasty for acute myocardial infarction: Every minute of delay counts. Circulation. 2004;109:1223-1225.

Fischell TA, et al. Initial clinical results using intracardiac electrogram monitoring to detect and alert patients during coronary plaque rupture and ischemia. J Am Coll Cardiol. 2010;56:1089-1098.
Gami AS, et al. Obstructive sleep apnea and the risk of sudden cardiac death: A longitudinal study of 10,701 adults. J Am Coll Cardiol. 2013;62:610-616.
Hunt SA, et al. 2009 focused update incorporated into the ace/aha 2005 guidelines for the diagnosis and management of heart failure in adults a report of the American college of cardiology foundation/American heart association task force on practice guidelines developed in collaboration with the international society for heart and lung transplantation. J Am Coll Cardiol. 2009;53:e1-e90.
International Searching Authority. International Search Report and Written Opinion for application PCT/US2019/013023, dated Mar. 26, 2019.
Jaana M, et al. Home telemonitoring for respiratory conditions: A systematic review. Am J Manag Care. 2009;15:313-320.
Javaheri S, et al. Occult sleep-disordered breathing in stable congestive heart failure. Ann Intern Med. 1995;122:487-492.
Jovanov E, et al. Thermistor-based breathing sensor for 491 circadian rhythm evaluation. Biomed Sci Instrum. 2001,37:493-497.
Kitsiou S, et al. Effects of home telemonitoring interventions on patients with chronic heart failure: An overview of systematic reviews. J Med Internet Res. 2015;17:e63.
Kristiansen NK, et al. Design and evaluation of a handheld impedance plethysmograph for measuring heart rate variability. Med Biol Eng Comput. 2005;43:516-521.
Leonard P, et al. An algorithm for the detection of individual breaths from the pulse oximeter waveform. J Clin Monit Comput. 2004;18:309-312.
Lindemann J, et al. Nasal mucosal temperature 493 during respiration. Clin Otolaryngol Allied Sci. 2002;27:135-139.
Lloyd-Jones D, et al. Heart disease and stroke statistics—2010 update: A report from the American heart association. Circulation. 2009;121 :e46-e215.
Logan AG, et al. Effect of home blood pressure telemonitoring with self-care support on uncontrolled systolic hypertension in diabetics. Hypertension. 2012;60:51-57.
Massumi RA, et al. Cardiac arrhythmias associated with cheyne-stokes respiration: A note on the possible mechanisms. Dis Chest. 1968;54:21-32.
Meischke H, et al. Reasons patients with chest pain delay or do not call 911. Ann Emerg Med. 1995;25:193-197.
Moody G, et al. Derivation of respiratory signals from multi-lead ecgs. Computers in Cardiology. 1985;12:113-116.
Mosa AS, et al. A systematic review of healthcare applications for smartphones. BMC Med Inform Decis Mak. 2012;12:67.
Myerburg RJ, et al. Sudden cardiac death. Structure, function, and time-dependence of risk. Circulation. 1992;85:12-10.
Oldenburg O, et al. Sleep-disordered breathing in patients with symptomatic heart failure: A contemporary study of prevalence in and characteristics of 700 patients. Eur J Heart Fail. 2007;9:251-257.
PEW research internet project. Mobile technology fact sheet. Http://www.Pewinternet.Org/fact-sheets/mobile-technology-fact-sheet.2014.
Pichon A, et al. Long term ventilatory adaptation and ventilatory response to hypoxia in plateau pika (ochotona curzoniae): Role of nnos and dopamine. Am J Physiol Regul Integr Comp Physiol. 2009.
Quaranta AJ, et al. Cheyne-stokes respiration during sleep in congestive heart failure. Chest. 1997;111:467-473.
Sayadi O, et al. An optimized method for estimating the tidal volume from intracardiac or body surface electrocardiographic signals: Implications for estimating minute ventilation. Am J Physiol Heart Circ Physiol. 2014,307: H426-436.
Sayadi, O., et al. "A Novel Method to Capture the Onset of Dynamic Electrocardiographic Ischemic Changes and its Implications to Arrhythmia Susceptibility." Journal of the American Heart Association: Cardiovascular and Cerebrovascular Disease 3.5 (2014).
Serizawa N, et al. Impact of sleep-disordered breathing on life-threatening ventricular arrhythmia in heart failure patients with implantable cardioverter-defibrillator. Am J Cardiol. 2008; 102:1064-1068.

(56) References Cited

OTHER PUBLICATIONS

Shelley KH, et al. The use of joint time frequency analysis to quantify the effect of ventilation on the pulse oximeter waveform. J Clin Monit Comput. 2006;20:81-87.

Siew ML, et al. Positive end-expiratory pressure enhances development of a functional residual capacity in preterm rabbits ventilated from birth. J Appl Physiol. 2009;106:1487-1493.

Smith JM, et al. Electrical alternans and cardiac electrical instability. Circulation. 1988;77:110-121.

Wang H, et al. A high resolution approach to estimating time-frequency spectra and their amplitudes. Ann Biomed Eng. 2006;34:326-338.

Weiss EH, et al. A novel lead configuration for optimal spatio-temporal detection of intracardiac repolarization alternans. Circ Arrhythm Eleetrophysiol. 2011;4:407-417.

Weiss EH, et al. An optimized method for the estimation of the respiratory rate from electrocardiographic signals: Implications for estimating minute ventilation. Am J Physiol Heart Circ Physiol. 2014;307:H437-447.

\* cited by examiner

FIG. 1B
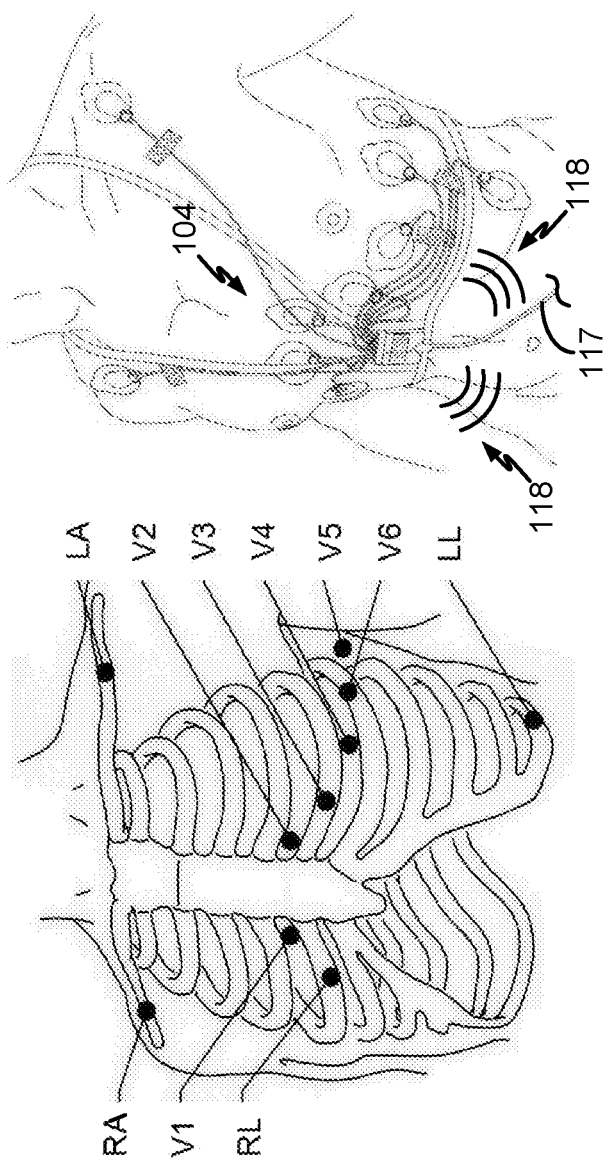
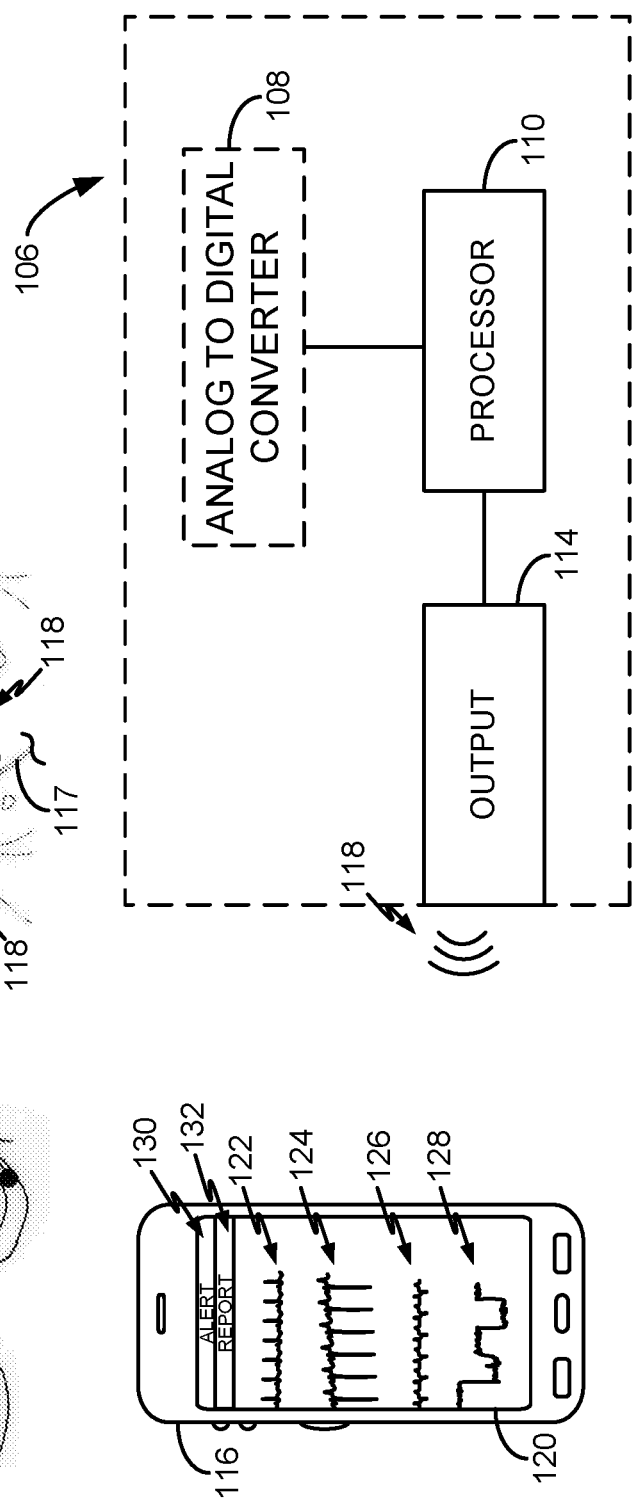

SYSTEM AND METHOD FOR PROCESSING CARDIAC SIGNALS AND PROVIDING REPORTS TO USERS REGARDING IMPENDING OR ONGOING MEDICAL CONDITIONS

CROSS-REFERENCE TO RELATED APPLICATIONS

The present invention represents the national stage entry of PCT International Application No. PCT/US2019/013023 filed Jan. 10, 2019, which is based on, claims priority to, and incorporates herein by reference in its entirety, U.S. Provisional Application Ser. No. 62/615,607, filed Jan. 10, 2018, and entitled "cvrPhone, a Novel Point-of-Care Smart-Phone Based System for Estimating the State of the Cardiac and Respiratory Systems."

STATEMENT REGARDING FEDERALLY SPONSORED RESEARCH

N/A

BACKGROUND

The present disclosure is related to subject monitoring. More particularly, the disclosure relates to systems and methods for determining impending or ongoing medical conditions using cardiac signals, such that a user, including the patient himself/herself, can receive a report or be alerted regarding the medical condition.

As chronic conditions are becoming more prevalent, there is a need to improve the effectiveness of disease prevention, to enhance access to healthcare and to sustain independent healthy living. Despite the availability of multiple evidence-based therapies for the treatment of heart failure (HF), its burden on the US population remains unacceptably high, with an estimated 1 million admissions per year. Moreover, HF readmission rates often correlate to a worsening prognosis and represent a significant healthcare expenditure for payers, despite efforts to reduce the burden of re-hospitalization using conventional markers.

Thus, there is a critical need to improve or radically change the processes and paradigms for assessing and/or treating chronic health conditions, such as HF and its many, many related conditions.

SUMMARY

The present disclosure overcomes the aforementioned drawbacks by providing a system and method for determining impending or ongoing medical conditions using cardiac signals, including using systems or hardware that are available for home use by a patient. In one non-limiting example the present disclosure provides systems and methods to utilize portable computing device, such as a cell phone or tablet, to detect or predict a variety of conditions. Such medical conditions may include myocardial ischemia (MI), abnormal respiratory events, such as periods of apnea and including respiratory sleep apnea (SA), and other conditions using electrocardiography (ECG) type monitoring or data.

In accordance with one aspect of the disclosure, a mobile computing system is provided that includes a communication connection configured to communicate with an elctro-cardiographic (ECG) apparatus configured to acquire ECG signals from the subject through a plurality of ECG leads. The system also includes a processor configured to receive the ECG signals through the communications connection and process the ECG signals to estimate at least one of a respiratory rate of the subject, a tidal volume of the subject, or an ischemic index of the subject from the ECG signals. The processor is further configured to generate an alert upon determining at least one of the ischemic index is above a threshold value or a change in respiratory rate or tidal volume indicative of an abnormal respiratory event. The system further includes a display configured to display the alert.

In accordance with another aspect of the disclosure, a method is provided for determining or predicting a medical condition of a subject from electrocardiographic (ECG) signals acquired from the subject. The method has steps including receiving, at a mobile computing device, ECG signals from an ECG monitor coupled to the subject through a plurality of ECG leads. The method also includes processing the ECG signals using the mobile computing device to estimate at least one of a respiratory rate of the subject, a tidal volume of the subject, or an ischemic index of the subject from the ECG signals. The method further includes generating an alert using the mobile computing device upon determining at least one of an ischemic index above a threshold value or change in respiratory rate or tidal volume indicative of an abnormal respiratory event.

In accordance with another aspect of the disclosure, a mobile computing system is provided that includes a communication connection configured to communicate with an elctrocardiographic (ECG) apparatus configured to acquire ECG signals from the subject through a plurality of ECG leads and a processor. The processor is configured to receive the ECG signals through the communications connection, process the ECG signals to estimate an ischemic index of the subject from the ECG signals, and generate an alert upon determining that the ischemic index is above a threshold value. The system also includes a display configured to display the alert indicating an impending cardiac event.

In accordance with yet another aspect of the disclosure, a mobile computing system is provided that includes a communication connection configured to communicate with an elctrocardiographic (ECG) apparatus configured to acquire ECG signals from the subject through a plurality of ECG leads and a processor. The processor is configured to receive the ECG signals through the communications connection, process the ECG signals to estimate at least one of a respiratory rate of the subject or a tidal volume of the subject, and generate an alert upon determining a change in respiratory rate or tidal volume indicative of an abnormal respiratory event. The system further includes a display configured to display the alert indicating a detected abnormal respiratory event.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1B is a schematic illustration of a system such as described in the present disclosure including a mobile device.

DETAILED DESCRIPTION

Figure 1A:
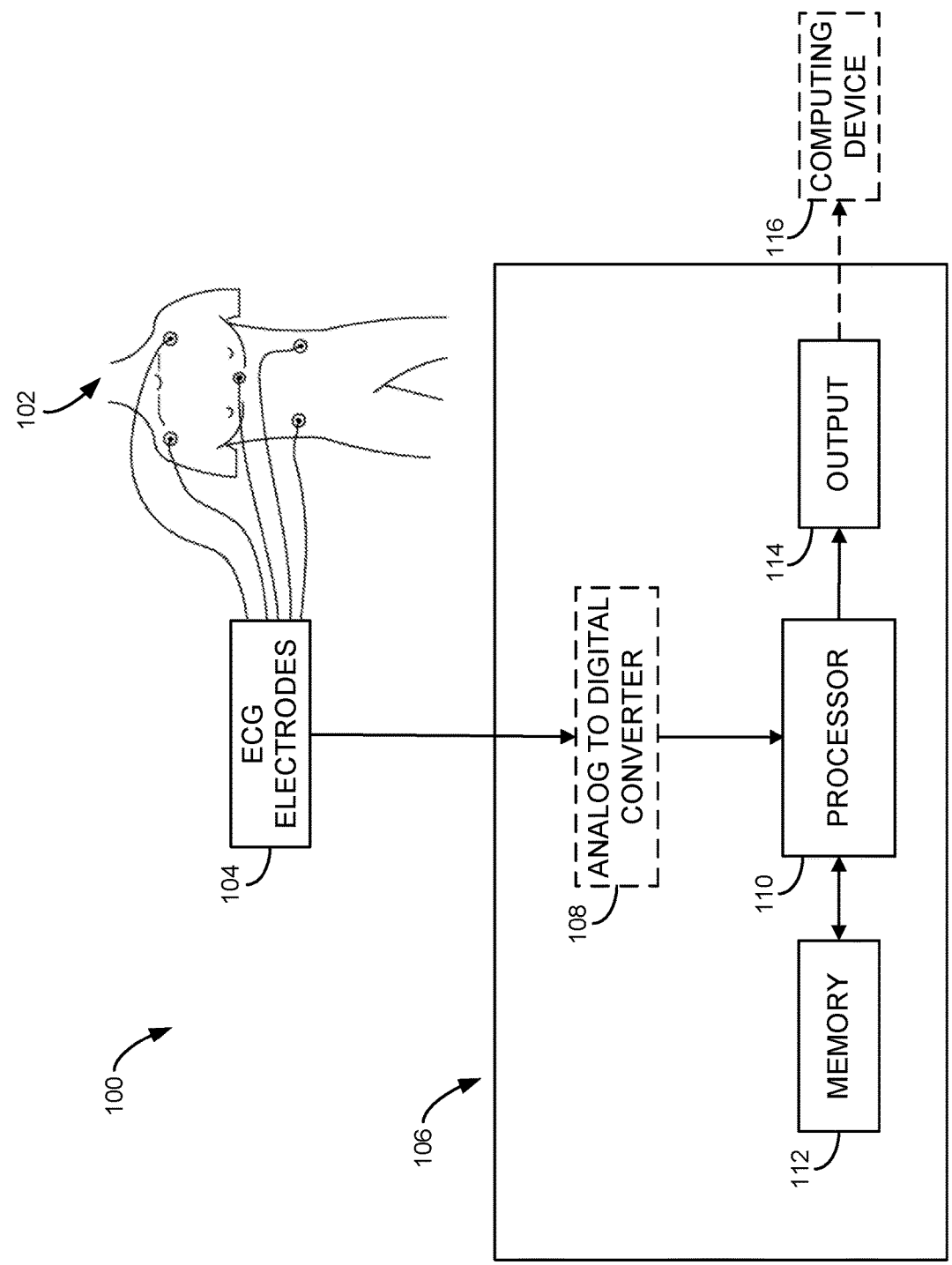
FIG. 1A is schematic illustration of an elctrocardiography (ECG) monitoring system configured in accordance with the present disclosure.

Turning to FIGS. 1A and 1B, an example for an ECG monitoring system 100 is shown, which may include a variety of systems or sub-systems and configurations that may include or operate as part of, or in collaboration with a computer, system, device, machine, or server, or may be or include a mobile, a wearable device (e.g., bracelet or watch), or portable or mobile computing device. As will be described in detail, the ECG monitoring system 100 may be or may include a computer, mobile phone, tablet, or other personal electronic device. The ECG monitoring system 100 may be or include a general computing device that is mobile or non-mobile that may integrate a variety of software and hardware capabilities and functionality.

The ECG monitoring system 100 can include a plurality of ECG electrodes that may be disposed upon a surface of, or within the anatomy of, a subject 102 according to a desired configuration to form part of an ECG electrode system 104. That is, the ECG monitoring system 100 may be designed to operate with surface electrodes or implantable electrodes, including those associated with pacemakers or defibrillators. In this regard, "ECG data" or "ECG signals" data may include data acquired from such surface or implanted or implantable electrodes and, thus, also includes intra-cardiac electrogram (EGM) data or EGM signals. The ECG electrode system 104 may include a traditional "12-lead" system, or may include substantially less electrodes.

Regardless of the configuration or number of the ECG electrodes in the ECG electrode system 104, the ECG signals from the ECG electrode system 104 are processed by a monitoring apparatus 106 and/or a computing device 116. The ECG monitoring apparatus 106 may be configured to convert ECG signals to digital ECG signals and, thus, include an analog-to-digital (A/D) converter 108. However, in some configurations, the leads/electrodes may individually digitize signals and, thus, the A/D converter is optional.

The ECG signals are communicated to a processor 110 of the monitoring apparatus 106 and/or computing device 116. Also, the apparatus 106 may include a memory 112, such that the ECG signals may be stored within and retrieved from a memory 112 or from an external location such as remote servers that may be in the cloud for analysis and/or communicated to an output 114. The output 114 may be a display or printing system or other system configured to generate a report. Alternatively, the output 114 may be a communications port for communicating data to the computing device 116.

Referring to FIG. 1B, in one non-limiting configuration, the ECG apparatus 106 may be used as an intermediary between the ECG electrode system 104 and the computing device 116. In this case, a wired connection 117 may be used to deliver ECG data from the ECG electrode system 104 to the ECG monitoring apparatus 106, or wireless signals 118 may be directed from the ECG electrode system 104 to the ECG monitoring apparatus 106. In this case, the output 118 of the ECG apparatus 106 may be a communications output, for example, that is configured to communicate information via wired or wireless signals 118 to the computing device 116. As illustrated in FIG. 1B, the computing device 116 may be a mobile computing system, including a smartphone, a wearable device (e.g., a bracelet or watch), or tablet.

Alternatively, in some non-limiting configurations, the ECG apparatus 106 may be omitted and the ECG electrode system 104 is configured to communicate directly to the computing device 116, such as via wireless signals 118 transmitted directly from the ECG electrode system 104 to the computing device 116. As will be described, the computing device 116 may be a mobile computing system, including a smartphone, a wearable device (e.g., a bracelet or watch), tablet, or other system configured to process the received data in the manner that will be described and communicate reports or alerts to a user, as will also be described. To this end, cardiorespiratory monitoring system (cvrPhone) is created that can be composed of three commercially available parts: an ECG module, a processor, and a Bluetooth module. As illustrated in FIG. 1B, the processor 110 may be part of an ECG monitoring apparatus 106, or may be part of the computing device 116, or a combination thereof.

As will be described in detail, the smartphone or other computing device 116 can estimate the respiratory rate (RR) and tidal volume (TV) based on the respiration-induced periodic fluctuations of ECG signals. Using this information or other information, further medical conditions or impending medical conditions can be determined or predicted. For example, abnormal respiratory events, such as apnea, and including sleep apnea (SA), can be determined using ECG-derived RR and TV analysis. Furthermore, Repolarization alternans (RA) has been implicated in the pathogenesis of ventricular arrhythmias and sudden cardiac death. As will be described, RA can be effectively estimated using surface lead electrocardiograms by analyzing beat-to-beat variability in ECG morphology using the systems and methods of the present disclosure. The system can estimate the ischemic state of a subject in real-time, from the ECG signals. In this way, systems and methods are provided to detect myocardial ischemia and/or arrhythmia susceptibility using a user-friendly, clinically acceptable, mobile platform.

In the illustrated, non-limiting example, a 12 lead ECG acquisition, display, and analysis system that formed by a 12-channel ECG module (such as a PSL-ECG 12MD form Physiolab) an AD converter 108 (such as an ADS1298 from Texas Instruments) a microcontroller or processor 110 (such as a Due from Arduino), an output 114 (such as a Bluetooth communications UART converter, such as a HC-05 from Guangzhou HC Information Technology Co., Ltd), and a mobile device (such as a smartphone) 116. In the illustrated, non-limiting 10 ECG electrodes (RL, LL, RA, LA, V1-V6) or more may be utilized. The A/D converter 108 can be configured to amplify and digitize the signals from the leads (I, II, and V1-V6), for example, simultaneously at 500 samples/sec (SPS). Wilson's central terminal ((LA+RA+LL)/3) may be used as a reference potential for the precordial leads. The processor 110 can communicate with the A/D converter 108 via, for example, a wired communications link or connection and coordinate communication of acquired data to the mobile device 116 via the output 114, such as using wireless communications protocols. Alternatively, the mobile device 116 may supplant the use of the monitoring apparatus 106. That is, the digitized 24 bit resolution signals may be transferred to the processor 110, which reduces the resolution to 16 bits in order to reduce the number of errors during wireless data transmission to the mobile device 116, or data may be directly sent from the electrode system 104 to the mobile device 116. In either case, the mobile device 116 may display the data trough a display and associated user interface 120. As such, the mobile device 116 may calculate the various ECG signals (I, II, III, aVR, aVL, aVF, and V1-V6), including a 12 lead signal from 10 leads. As illustrated, the user may select to display multiple leads at any given time 122-126 and/or may view the respiration rate 128, as well as alerts 130 or notices and reports 132.

As will be described, the processor 110 or mobile device 116 is configured to process the data in accordance with the present disclosure and report back to or provide alerts to users, local or remote, including the subject 102. In some configurations, the processor 110 or processor of the mobile device 116 may be capable of determining a variety of medical conditions or indicators of medical conditions.

Figure 1C:
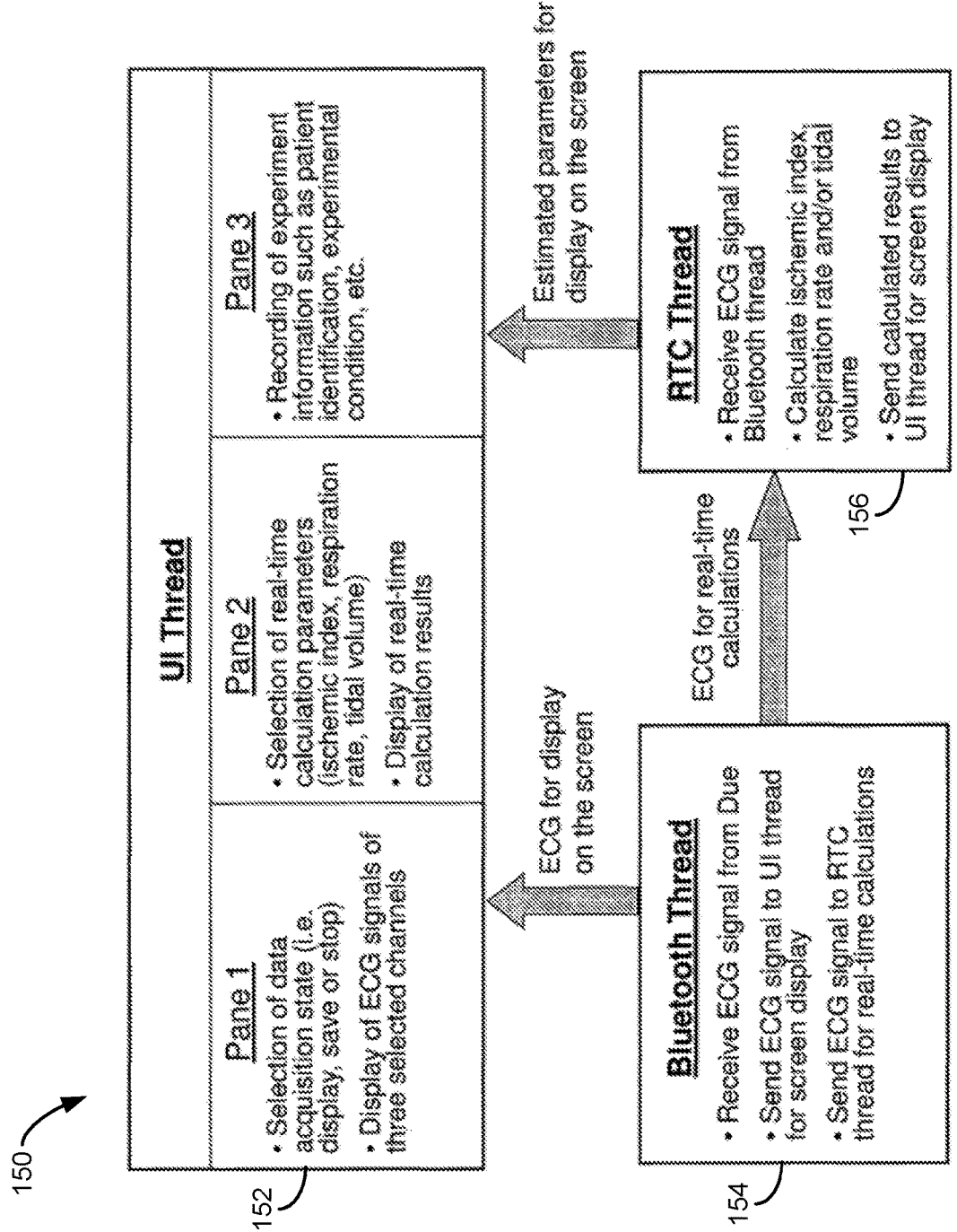
FIG. 1C is a block illustration of a software architecture for operating a mobile device in accordance with the present disclosure.

In one non-limiting implementation, a smartphone was used as the computing device 116. A custom application was developed to run on the smartphone. As illustrated in FIG. 1C, the application 150 for the smartphone included three threads that included a user interface (UI) thread 152, a communications (as a non-limiting example, a Bluetooth) thread 154, and real-time calculation (RTC) thread 156. The UI thread 152 can include three panes. Pane 1 displays ECG signals of three selected leads. Pane 2 displays real-time estimation values of respiration rate (RR), tidal volume (TV), and ischemic index. As will be described, other parameters and/or calculations may also be displayed. Pane 3 is used to record study notes. The Bluetooth thread 154 receives ECG signals from the ECG acquisition device, and sends the signals to the UI thread 152 for display on pane 1 and to the RTC thread 156 for realtime calculations. The RTC thread 156 also sends calculation results to the UI thread 152 for display on pane 2.

As one non-limiting example of a process that can be carried out on the above-described systems, the assessment of the RR and tidal volume (TV) can provide an important piece of information in Cheyne-Stokes respiration (CSR) in heart failure (HF) or a variety of other conditions. Cheyne-Stokes respiration has been identified in up to 40% of patients with chronic HF and has been associated with cardiac dysrhythmias. Additionally, CSR is a marker of a negative prognosis and increased mortality in HF patients, while improvements in CSR serve as a positive marker of HF response to medical therapy. Furthermore, in patients with ischemic heart disease, recent evidence suggests that monitoring changes to the ST-segment of an ECG signal to detect acute closure of a coronary artery can lead to a reduction in symptom-to-door time and, thereby, potentially improve clinical outcomes in the setting of acute coronary syndromes.

These clinical observations highlight the need for tools to monitor respiratory and cardiovascular parameters in ambulatory patients with heart failure and coronary disease, without the need for specialized hardware that may restrict mobility. The systems and methods of the present disclosure provide tools and resources to assess and/or report on medical conditions, such as coronary ischemia and measure the RR and TV using, for example, body surface ECG signals only, which can be recorded and analyzed by a smartphone or other user-friendly and available device.

Figure 2:
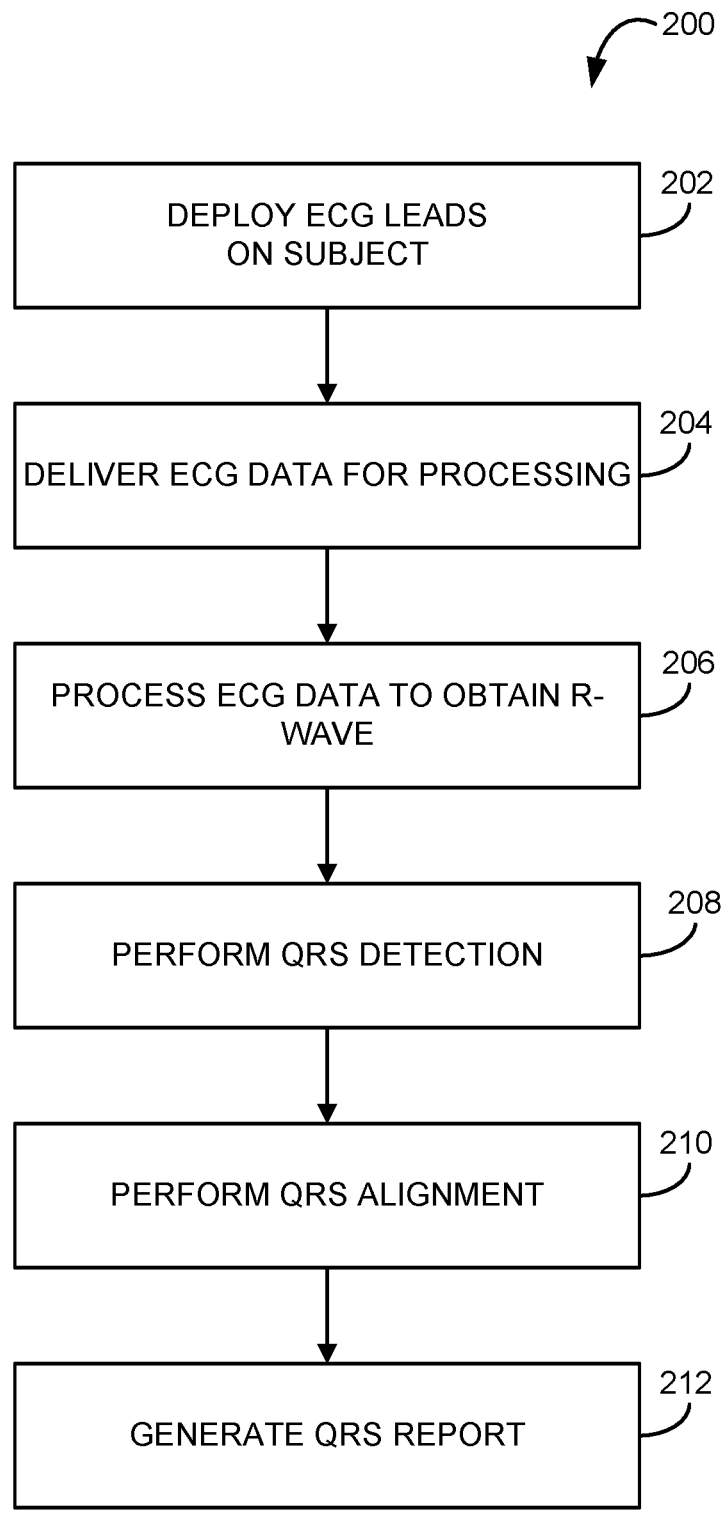
FIG. 2 is a flowchart setting forth steps of an exemplary operation of the systems of FIGS. 1A-1C in accordance with the present disclosure.
Figure 3:
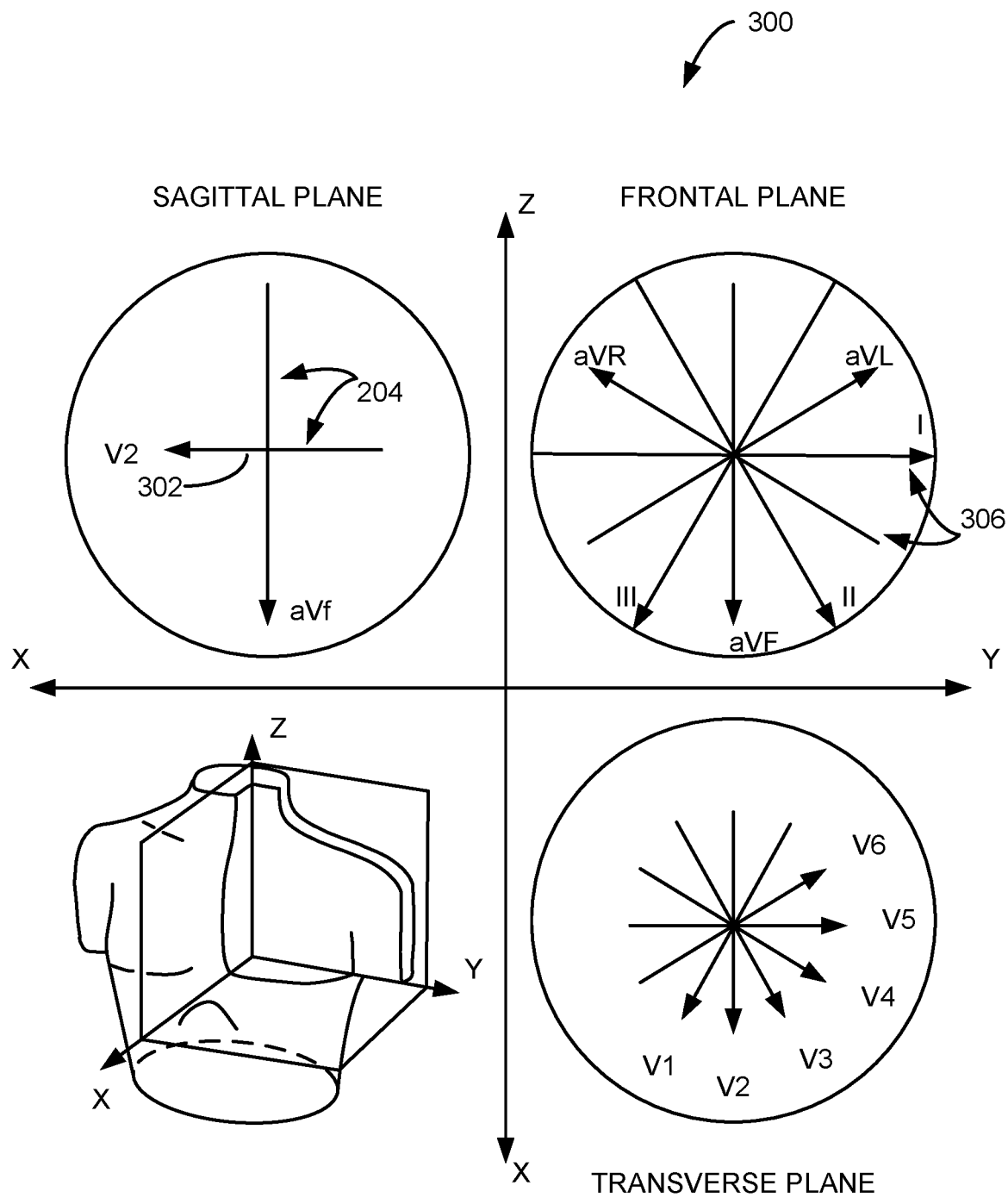
FIG. 3 is a schematic diagram showing a standard, 12-lead ECG configuration for use in accordance with the present disclosure.

In one configuration and with reference to FIG. 2, a software-based QRS detection process 200 is provided to process data received from a given lead. As is well-known in the art, an ECG lead may typically refer to the tracing of the voltage difference between two ECG electrodes, wherein the naming of an ECG lead in a particular configuration makes reference to the electrical polarity and placement location of the ECG electrodes. Signals from ECG leads may be obtained from explicit measurement of voltage difference between two physical ECG electrodes, known in the art as bipolar ECG leads, or measurement of voltage differences between a single physical ECG electrodes and combinations of signals from other ECG electrodes. Referring to FIG. 3, a 12-lead ECG configuration 300 is illustrated, which is a configuration common in clinical use. A given direction along an ECG lead 302 is known in the art as a lead axis. As shown in FIG. 3, lead axes may be orthogonal 304 (i.e., oriented substantially perpendicular to one another) and other lead axes may be non-orthogonal 306.

Most ECG monitoring system and methods require and/or assume that particular combinations of ECG leads will be arranged orthogonally because an orthogonal relationship between combinations of leads provides optimal signal strength, typically calculated as a signal-to-noise ratio (SNR). As such, traditional ECG systems require operators or clinicians to specifically configure combinations of ECG leads to be arranged orthogonally. For example, many ECG monitors expect a SNR achievable only with substantial (i.e., within a few degrees) orthogonality or such ECG monitors may base calculations upon a specific assumption of orthogonality. For example, when the leads are orthogonal, the arctangent of the ratio of the QRS areas measured in the two leads results in the angle (theta) of the mean axis with respect to one of the lead axes. A lack of orthogonality results in diminished results or inaccurate calculations.

In particular, with reference to FIG. 3, orientation of a 12-lead ECG system typically provides spatial information about the heart's electrical activity in three orthogonal directions: left/right, superior/inferior, and anterior/posterior. Each of the 12 leads represents a particular orientation in space, as indicated below (RA=right arm; LA=left arm, LL =left foot). Bipolar limb leads (frontal plane) include Lead I-RA (−) to LA (+) (Right Left, or lateral); Lead II-RA (−) to LL (+) (Superior Inferior); and Lead III-LA (−) to LL (+) (Superior Inferior). Augmented bipolar limb leads (frontal plane) include Lead aVR -RA (+) to [LA & LL] (−) (Rightward); Lead aVL-LA (+) to [RA & LL] (−) (Leftward); and Lead aVF-LL (+) to [RA & LA] (−) (Inferior). Finally, bipolar chest leads (horizontal plane) include Leads V1, V2, V3: (Posterior Anterior) and Leads V4, V5, V6: (Right Left, or lateral). Thus, within each of these various and common ECG lead configurations, there are various lead combinations that represent lead combinations presumed to be orthogonal. A failure to maintain the requisite orthogonality of these lead combinations presumed to be orthogonal or between traditionally-orthogonal groups or pairs of leads that are dictated and assumed to be orthogonal in a given lead configuration is considered unfavorable for the reasons explained.

However, the present disclosure recognizes that a combination of ECG leads from the plurality of ECG leads can be determined that provides a desired or optimal SNR above a threshold value. Thus, even with less than a 12 lead system, the systems and methods of the present disclosure can process the ECG signals from a combination of ECG leads to extract a respiratory rate of the subject from the ECG signals. Based on the determined SNR, the present disclosure can compensate for or calibrate for non-orthogonality and, using the information provided by such lead combinations, provide an ECG-derived respiration measurement surrogate, such as described in U.S. patent application Ser. No. 15/111,638, which is incorporated herein by reference in its entirety for all purposes. In this regard, there is no need to predefine a lead configuration and, within a predefined lead configuration known to include lead combinations presumed to be orthogonal, allows such traditionally-orthogonal groups or pairs of leads to be non-orthogonal.

Furthermore, some have determined that an ECG-derived respiration can be derived by using an estimation of the mean cardiac axis on a beat-by-beat basis, and deriving a respiration rate (RR) from this signal as the mean cardiac axis changes throughout the respiratory cycle. Specifically, as mentioned above, the angle of the mean cardiac axis with respect to one of the lead axes may be estimated by calculating the arctangent of the ratio of QRS amplitudes from two ECG leads. This respirophasic modulation is independent of electrode motion artifact or other sources of non-specific noise. The respiration frequency can then be estimated from the respirophasic signal using a spectral analysis method.

The present disclosure recognizes that it is often impractical to select orthogonal intracardiac leads, both because the identification of orthogonal ECG leads is very difficult, even under fluoroscopy, and because lead motion may cause the angle between two leads to change as a function of respiration or posture. In addition, not only the mean cardiac axis but also the thoracic impedance changes as a function of respiration, such that the angle of the mean cardiac axis is not perfectly described by the arctangent of the ratios of orthogonal leads. Therefore, the current disclosure recognizes that one can accurately and reliably estimate the respiration rate from non-orthogonal ECG lead combination, and without calculating the arctangent of the QRS ratios, as also described in U.S. patent application Ser. No. 15/111,638, which is incorporated herein by reference in its entirety for all purposes.

Returning to FIG. 2, after the ECG leads are deployed onto the subject at process block 202, at process block 304, data is acquired by the ECG leads and delivered for processing. At process block 206, the ECG data, such as from even just one lead, is processed to obtain preliminary R-wave annotations. With the R-WAVE annotated, a preliminary QRS detection is performed at process block 208. The preliminary QRS detections can be used to identify abnormal beats (as a non-limiting example, premature ventricular complexes and/or aberrantly conducted beats) using a template-matching QRS alignment technique at process block 210.

To perform the QRS detection and alignment, in one non-limiting example, for each new beat, a window (as a non-limiting example, an 80 msec window) can be centered at the peak of the QRS complex formed from the preliminary QRS detection at process block 308. Then, an isoelectric PR segment can be subtracted as a zero amplitude reference point. This can be done by estimating the mean voltage in a window (as a non-limiting example, a 10 msec window) preceding the start of each QRS complex. A median QRS template can be generated from all "normal" QRS complexes across the previous beats (as a non-limiting example, 31 beats) and the beat can be aligned to the QRS template, as a non-limiting example, using cross-correlation. In some configurations, cross-correlation or other processing can be repeated multiple times (as a non-limiting example, twice or three times) for each new QRS complex to ensure proper QRS alignment. A beat can be considered "abnormal" if its correlation coefficient is less than a threshold value. As a non-limiting example, a threshold value of 0.90 can be used. Additionally or alternatively, the beat can be considered "abnormal" if the preceding R-to-R (RR) interval was at least a predetermined percentage shorter (as a non-limiting example, 10% shorter) than the mean RR interval of the previous beats, such as across 7 beats, as a non-limiting example.

Also, the present disclosure recognizes that the apex of the heart is stretched towards the abdomen during inspiration, and compressed towards the breast during expiration. In addition, filling and emptying of lungs changes distribution of the thoracic impedance. Therefore, the present disclosure recognizes that respiration generates movement of the heart and change of the thoracic impedance, which cause periodic amplitude modulation of the ECG signals. To process the data, the root mean square (RMS) values of the ECG signals can be processed to extract this periodic modulation. That is, the RMS value of each beat in a window (as a non-limiting example, an 80 msec window may be used) centered at the peak of the QRS complex can be calculated. The derived RMS envelope exhibited periodic oscillation.

The QRS alignment at process block 210 may be optional. Whether performed or not QRS alignment is performed at process block 210, a QRS report is generated at process block 212. The report may be a real-time delivery of a QRS waveform, or may include further information, such as annotation and the like. The report or information from the report may be displayed or otherwise communicated, and/or the report may be used for further processing, as will be described.

QRS boundaries can also be detected using the above method, for example as part of the QRS detection process 208. In one non-limiting example, QRS boundary detection may be performed using an initial window extending from an initial predetermined value prior to the QRS detection point to either an additional predetermined value after the QRS detection point or to the beginning of the T-wave. In one non-limiting example, QRS boundary detection may be performed using an initial window extending from 50 msec prior to the QRS detection point (as an example of the initial predetermined value) to either a 80 msec after the QRS detection point (as an example of the additional predetermined value) or to the beginning of the T-wave. In one non-limiting example, the selection between using the second predetermined value and the beginning of the T-wave may be achieved by selecting whichever is desired or shorter.

Once QRS detection is performed, for example, as described with respect to FIG. 2, other processing and analysis may be performed. For example, in one non-limiting example, respiration rate (RR) and tidal volume (TV) estimation can be performed. Regarding estimations of RR, systems and methods may be utilized such as described in U.S. patent application Ser. No. 15/111,638, which is incorporated herein by reference in its entirety for all purposes.

In addition, the present disclosure recognizes the effect of the percentage of premature ventricular contractions (PVCs) in estimating the respiration rate (RR). That is, in one study, the RMS amplitude for all abnormal beats was obtained from neighboring RMS values using cubic-spline interpolation. By replacing aberrant beats with interpolated points, rather than the RMS values of the average good beats, discontinuities in the RMS ratio sequence was controlled or even minimized prior to spectral analysis. Two different approaches were utilized to determine the effect of PVCs on estimating RR: (i) interpolation of the RMS signal, or (ii) interpolation of the RR. In the presence of PVCs, interpolation of the RR exhibits a smaller rate increase of the error. Instead of determining the RMS value of an abnormal beat using cubic spline interpolation of normal beat RMS values, particularly under quasi-static conditions during which the RR remains relatively constant, the RR estimation algorithm can be modified so that, if there are more than a predetermined amount (as one non-limiting example, 10%) abnormal beats in the window (as one non-limiting example, a 32 beat window), then the corresponding RR is interpolated using the cubic spline method.

In addition to RR, TV can be estimated. Regarding estimations of TV, systems and methods may be utilized such as described in U.S. patent application Ser. No. 15/111,638, which is incorporated herein by reference in its entirety for all purposes.

Given that the TV estimation from ECG signals relies on respiration-induced modulation of the QRS complex amplitude, opportunities for improving the above techniques for estimating TV were developed. First, the respiratory envelope was estimated by calculating the beat-to-beat, root-mean-square (RMS) of the QRS complex of each lead. Then, the percent modulation (PM) that normalized peak-to-peak amplitude of respiratory envelope was estimated, as a surrogate for TV, where PM is defined as 100 (%)×(max envelope−min envelope)/(max envelope+min envelope)/2 of each cycle of the respiratory envelope. In a prior study, the maximum PM value among all leads was used to estimate the TV at each cycle of respiratory envelope and then a model was developed that provides the TV from PM, as follows: TV=a×PM+_b, where coefficients a and b were derived from a least square regression analysis from studies.

Alternatively, the least square regression analysis can be applied using multiple different methods (including the previously used maximum PM method), to improve the accuracy of TV estimation from body surface ECG signals. Thus, referring to FIG. 4, the above-described techniques for determining TV can be optimized, such as for a given set of ECG leads or processing on a mobile device, such as described above. As will be described, two optimization techniques can be utilized, which can be differentiated based on the optimization parameter utilized: (i) the PM or (ii) the peak difference (max envelope−min envelope), PD. A variety of methods utilizing these techniques may be used with the present disclosure.

The first technique selects the lead with the median PM, and uses the PM for TV estimation. The second method selects the lead with the maximum PM, and uses the PM for TV estimation. The third and fourth methods are identical to the first and second ones respectively, but this time the PD is used instead of the PM. The fifth method selects the lead with maximum PD, but uses the PM for TV estimation.

Finally, a sixth method selects the lead with maximum PM, but uses the PD for TV estimation.

Tests were performed using each of these methods. ECG data (n=10) was used to obtain the slope and the intercept for each of the six different methods respectively, and estimate the TV (TV=a×PM(PD)+b), using the least square analysis. The error between the estimated and the true TV for each of the six methods was compared. The normalized (by the true TV) mean squared error (MSE) and the coefficient of variation (CV), defined as $\sigma/\mu$; where, $\sigma$ and $\mu$, are the standard deviation and the mean respectively of the estimated TV. Although for the TV estimation, ECG signals were acquired at 0, 250, 500 and 750 ml TVs, 0 ml was excluded, because M8E cannot be normalized by 0 ml and CV cannot be defined at 0 ml. On average, over the three TVs, the first method (median PM) exhibited the smallest NMSE and CV values. Thus, in some configurations and studies, this method for the TV estimation was utilized.

Figure 4:
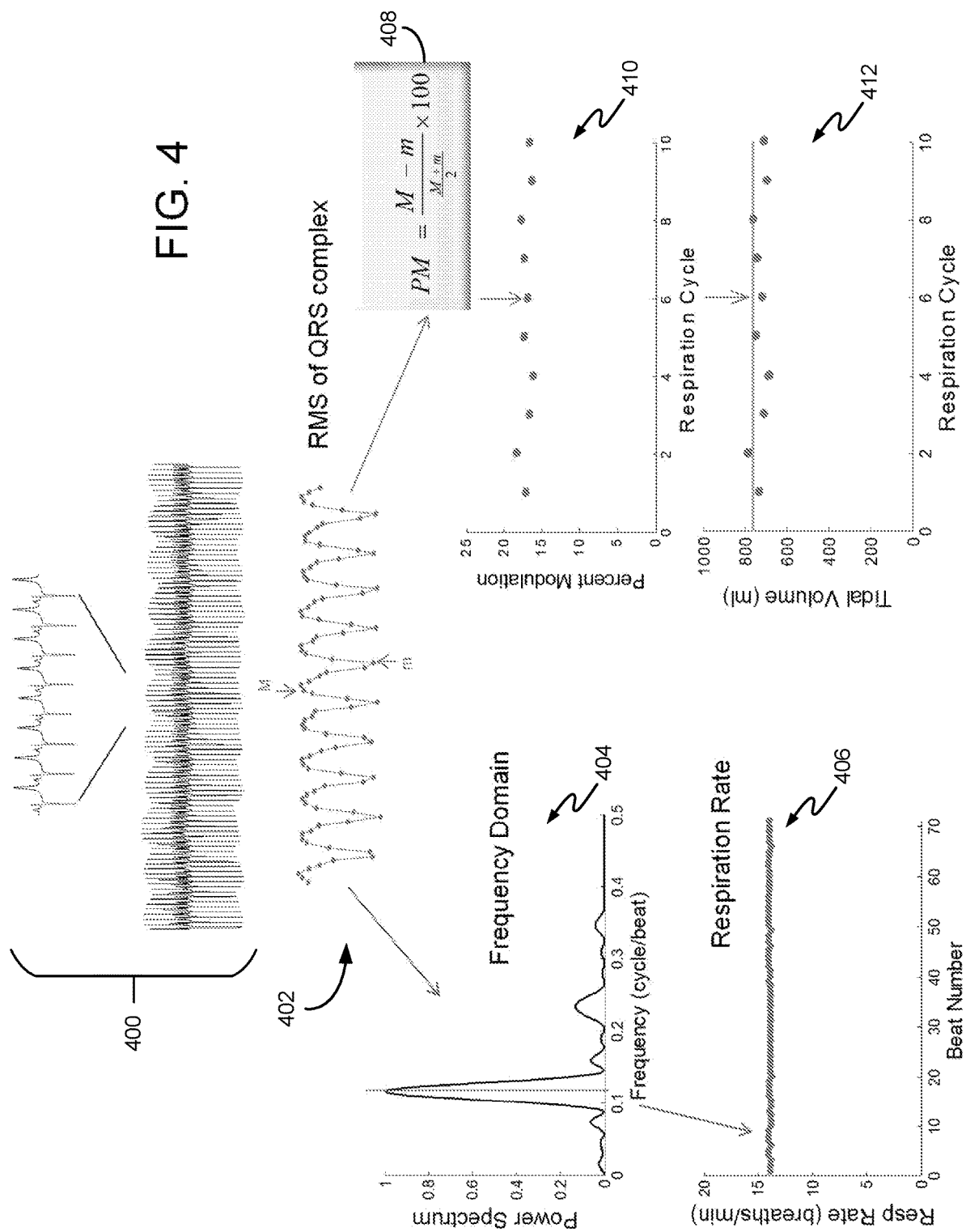
FIG. 4 is a flow diagram setting forth steps of an exemplary process for derive respiratory information and/or tidal volume information in accordance with the present disclosure.

Referring to FIG. 4, some non-limiting examples steps of one example of a method for performing the RR and TV estimation is presented. Raw ECG data 400 was acquired. To extract the respiration-induced periodic modulation of the ECG signals, the root mean square (RMS) value of the ECG signal was estimated, on a beat-by-beat basis, in a window centered at the peak of the QRS complex 402, as described above, where the window may be a 100 ms in duration.

The respirophasic signal for lead pairs can then be calculated as the RMS signal ratio on a beat-by-beat basis. Specifically, each lead pair combination consisted of a test lead (the numerator), and a reference lead (the denominator). For each ECG lead pair, the respirophasic signal can be calculated as the multi-beat (e.g., 32 beat) length RMS signal ratio on a beat-by-beat basis. The power spectrum of the RMS ratio data can be calculated using a Fourier transform (e.g., 512-length) to improve the frequency-domain resolution, as illustrated at graph 404. The dominant power spectral peak (e.g., between 0.03 and 0.3 cycles/beat) can be detected, and the signal-to-noise ratio (SNR) can be calculated, as the spectral peak power divided by the mean of the power spectrum from 0 to 0.5 cycles/beat, expressed in decibels:

$$SNR = 10\log_{10}\left(\frac{\text{signal}}{\text{noise}}\right).$$

In one non-limiting example, SNR values were calculated for every combination of lead pairs, and the pair with highest SNR was selected for RR estimation across all 144 permutations. In any case, the selected peak frequency in cycles/beat can be converted to breaths per minute by scaling the frequency by the average heart-rate (HR) across a beat window (e.g., a 32 beat window), as illustrated at graph 410. As described, if there are more abnormal beats in the beat window than a threshold value (e.g., greater than 10%), then the corresponding RR can be linearly interpolated. A frequency in the Fast Fourier Transform spectrum that is smaller than a threshold cycles per heart beat (e.g., 0.03) can be considered to be an abnormal respiratory event (as will be further described), and a zero assigned to the corresponding RR estimation.

Turning to the other calculation path of FIG. 4, TV can be estimated using the peak-to-peak amplitude of the respiratory RMS signal, as described above. To account for cases of high RR and low HR, which could effect the accuracy of the peak-to-peak estimation of the RMS signal, a cubic spline interpolation can be used to double the number of the RMS signal samples. Subsequently, the peak-to-peak amplitude of the respiratory envelope can be normalized to the mean value to obtain the percent modulation (PM), as indicated by equation 408.

Then, the median PM can be found from all leads in a running window (e.g., 10 second windows), as illustrated in graph 410. A regression equation can be applied on the median PM to estimate the corresponding TV, as illustrated in graph 412. When the estimated TV is negative, the value can be set to zero.

As described, accurate measures of RR and TV, along with the accurate QRS reports, provides user with resources that are valuable in a variety of care settings, including ambulatory care, emergency care, home care, self care, long-term care, and the like, particularly, when extended to operating on a mobile device. Some non-limiting examples include determining or predicting ischemia and predicting arrhythmia. Other non-limiting examples include abnormal respiratory events, such as apnea, and including sleep apnea.

Ischemia

Ischemia detection is another analysis that can be performed utilizing the systems and methods of the present disclosure. Systems and methods may be utilized such as described in U.S. Pat. No. 9,949,659, which is incorporated herein by reference in its entirety for all purposes.

Figure 5:
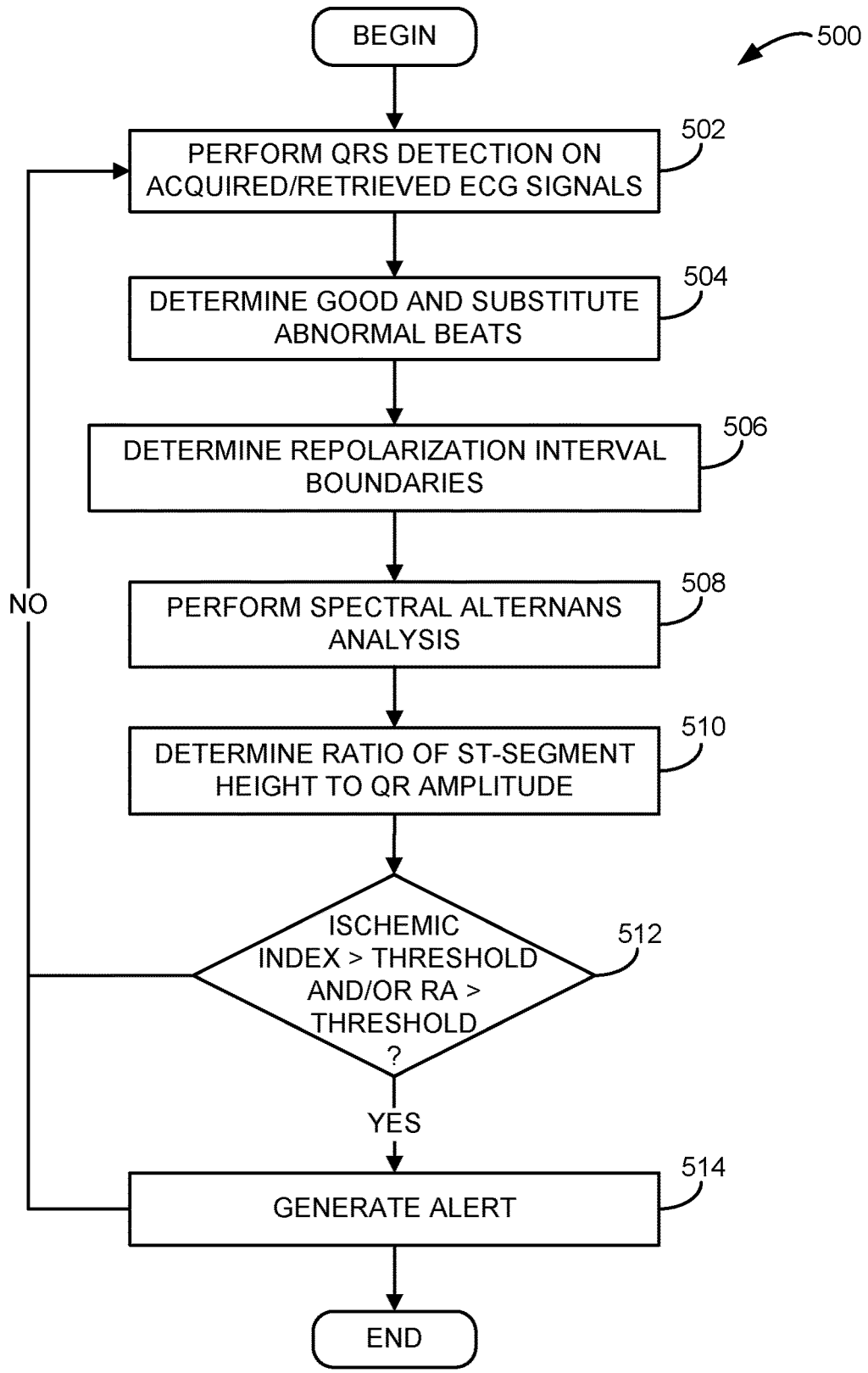
FIG. 5 is a flowchart setting forth steps of an exemplary process for determining ischemic events or arrhythmic events in accordance with the present disclosure.

One non-limiting example of an ischemia detection process 500 is illustrated in FIG. 5. Specifically, preliminary R-wave time-points (or beats) may be obtained using the above-described QRS detection algorithm at process block 502, which may include using the template-matching QRS alignment algorithm described above at process block 504. Specifically, at process block 504, abnormal beats can be identified in a beat sequence of a desired length (e.g., 128 beats) and each abnormal beat can be substituted with a median odd or even template beat on a lead-by-lead basis (e.g., estimated from the odd or even "normal" beats respectively in the 128 beat sequence), depending on whether the abnormal beat is an odd or an even beat.

Then, at process block 506, repolarization interval boundaries for repolarization alternans (RA) analysis can be determined, for example independently determined, for each of the body surface leads, due to variability in the morphology and timing of the T-wave between leads. Briefly, the power method identifies the onset/offset points at time points corresponding to thresholds (e.g., 5% and 95% of the cumulative sum of the signal power).

At process block 508, spectral alternans analysis can be performed on a beat-by-beat basis for each multi-beat data sequence using a multi-point power spectrum (e.g., 512 point) to improve the frequency-domain resolution. To account for the spatial variability of RA, spectral analysis can be independently performed for each lead. Repolarization alternans indices can be estimated as follows:

$$\text{alternans voltage } (\mu V) = \sqrt{\text{alternans peak} - \mu_{noise}} ;$$

$$K_{score} = \frac{\text{alternans peak} - \mu_{noise}}{\sigma_{noise}};$$

where, the alternans peak is the peak in the aggregate power spectrum corresponding to 0.5 cycles/beat and the mean ($\mu_{noise}$) and the standard deviation ($\sigma_{noise}$) of spectral noise are estimated from a predefined aggregate power spectrum noise window (e.g., 0.43-0.46 cycles/beat). The alternans voltage is a direct measure of the presence of alternans while the alternans $K_{score}$ is a measure of the statistical significance of the alternans voltage. Thus, at process block 508, for each lead, alternans can be estimated on a beat-by-beat basis using a rolling 128-beat window that was shifted one beat at a time.

Elevation/depression of ST-segment has been shown as a strong marker of myocardial infarction (MI). At process block 510, an ischemic index can be defined as the absolute value of the ratio of integral of the ST segment to the QR amplitude. The ST integral can be conceptualized as the mean amplitude calculated over the whole ST-segment above or below the isoelectric baseline, when the polarity at both ends of the ST-segment is the same. If the polarity is opposite, then the longer segment is selected for the ST height calculation.

For the estimation of the ischemic index, the above-described T-wave boundaries can be detected lead-by-lead by performing linear baseline adjustment across the T-wave window (using the approximate T-wave boundaries described above), squaring the T-wave, integrating the T-wave power, and determining new and more accurate T-wave boundaries at timings corresponding to 1% and 99% of the signal power, respectively.

At decision block 512, the ischemic index determined at process block 510 is compared to a threshold value and/or the repolarization alternans analyzed at process block 508 is compared to a threshold. If the ischemic index is greater than its threshold value and/or the repolarization alternans is greater than its corresponding threshold, an alert or report may be generated at process block 514. As one non-limiting example, the threshold value may be selected based on clinical guidance, or monitoring needs. As one non-limiting example an ischemic index that is more than three times the mean baseline value for a specific lead may serve as the threshold for triggering the alert. As one non-limiting example of the threshold for considering the RA, for example, an alternans voltage greater than 1 µV and a $K_{score}$ greater than 3. On the other hand, if the ischemic index and/or the RAs is below the threshold value at decision block 512, the process iterates to continue analyzing.

Ischemia-Related Studies

Regarding the ischemic index, further studies were performed using lead V6 following an ischemic event (time 0 min). From this analysis, the ischemic index was observed to start increasing abruptly about 75 sec after the occlusion. A 1 min running median of the ischemic index values was presented, which displays a smooth curve that exhibits an ~30 sec delay with respect to the timing of the beat-by-beat ischemic index values. Within two minutes from occlusion, the ischemic index was observed in the majority of body-surface leads and became significantly (p<0.05) higher compared to baseline. In 3 MI cases, tachycardia developed 294±166 sec after the coronary artery occlusion, which was preceded by significant increases of the ischemic index for about 1, 4 and 1 min, respectively. ECG signals (leads II, AVF, V6) can be used, such as during the transition from sinus rhythm to ventricular tachycardia after coronary artery occlusion, to generate alerts for timely delivery of therapy and even prevention of sudden cardiac death.

Arrhythmia susceptibility, under varying states of RA, was assessed using programmed ventricular stimulation (PVS), in which a positive outcome was defined as sustained VT or VF lasting >30 secs or requiring external defibrillation.

Briefly, percutaneous vascular access was obtained in the jugular veins and femoral arteries and veins using standard Seldinger techniques. Decapolar catheters were placed under fluoroscopic guidance in the right atrium (RA), right ventricle (RV), coronary sinus (CS), and left ventricle (LV). An inferior vena cava catheter was inserted as a reference electrode for unipolar signals.

In order to quantify the outcomes of PVS across different RA states, a single "score" rank parameter (Srank) was developed that assigned the highest score (highest arrhythmia susceptibility) to the intervention that required (i) the smallest number of extra-stimuli during PVS to induce an arrhythmia, or (ii) if the number of extra-stimuli is the same, when the coupling interval between S1 and $S_{last}$ is the smallest, both of which suggest less aggressive stimulation was necessary to induce sustained VT/VF reflecting a more vulnerable arrhythmic substrate. There is no single best validated clinical method to assess arrhythmia susceptibility in a fully quantifiable manner. The $S_{rank}$ score was developed not as surrogate of VT/VF (with a binary outcome), but rather as a method to obtain a quantitative relationship between the level of RA and the likelihood of inducing VT/VF.

Pacing pulses during PVS were delivered from LV15 and had amplitude and duration 50 mA and 2 msec, respectively. PVS was initiated with a drive train of 8 beats (S1) at a cycle length of 400 milliseconds (ms) with an extra-stimulus (S2) delivered at a coupling interval of approximately 300 ms. The coupling interval for S2 was reduced in 10 ms steps until ventricular refractoriness was reached, at which point S2 was fixed at 20 ms above the point of refractoriness and an S3 was added beginning at a coupling interval 10 ms less than S2. This process was repeated until sustained VT/VF was induced or ventricular refractoriness was reached on S6, in which case PVS was deemed non-inducible under those conditions.

Programmed ventricular stimulation was performed in the absence and presence of triggered pacing to suppress RA. If sustained VT/VF was induced, biphasic external defibrillation was performed using 150 joules with paddles placed on the chest of the animal and a rest period of ~10 min was allowed after each positive PVS.

Aggregate variables were expressed as mean±standard deviation. Box-plot representation including the median, 90-10% and 95-5% percentiles was used to demonstrate statistical properties of the estimated data sequences with/without RA. For each RA parameter, a baseline value for each recording was obtained by estimating the mean value of that parameter over a time interval of 2 to 4 min before occlusion. Then, the respective baseline value was subtracted from all estimates of that parameter for that particular recordings starting from 1 minute before occlusion. Comparisons were then made for the alternans noise, voltage and $K_{score}$ across leads between a minute before occlusion and each subsequent min, using the signed rank test and the highest p-value across leads for each of the alternans noise, voltage, and $K_{score}$, is reported. A p value of <0.05 and an "*" was used to determine statistical significance; a "+" was used to indicate 0.05<p<0.1.

Smartphone-based repolarization alternans estimation yielded results (n=29 records, N=17 animals) of coronary artery occlusion induced temporal changes of the estimated RA (that involves both the ST-segment and T-wave) indices. Across all 12 ECG leads a significant change (p<0.05) of the alternans noise, voltage and $K_{score}$ after occlusion, compared to before occlusion, was observed.

Repolarization alternans before a tachy-arrhythmic event were observed in ECG signals (lead V3) during the transition from sinus rhythm to ventricular tachycardia after coronary artery occlusion. Such information can be used by the above-described system to alert a physician and/or a patient and result in timely delivery of therapy and perhaps prevention of sudden cardiac death.

Results reflecting temporal changes of the alternans indices were observed during myocardial infarction in which coronary artery occlusion led to spontaneous ventricular fibrillation (n=4 records; N=4 animals). The alternans noise level was statistically different (p<0.05) before and after occlusion, across all 12 ECG, and also ischemia leaded to a statistically significant increase of the alternans voltage (p<0.05) and $K_{score}$ (p<0.05) after occlusion, compared to before occlusion.

The burden for repolarization alternans was significantly higher during MI than at baseline. The alternans burden (%) before and after coronary artery occlusion during MI (n=29 records; N=17 animals) was studied. The incidence of RA was evaluated beat-by-beat basis, and the RA burden was evaluated as a percent of sequences that exhibit significant RA. The RA burden was estimated separately after the occlusion separately, for each record. During MI, the RA burden was significantly higher (p<0.05, using the paired t-test) compared to baseline.

Furthermore, the relationship of repolarization (ST-segment and T-wave) alternans vs ischemic index during myocardial infarction and preceding VT/VF was explored. For both the alternans voltage (p<0.05) and $K_{score}$ (p<0.05, using the paired t-test), the constant of the exponential model is significantly smaller before VT/VF, indicating that RA manifests a profound arrhythmogenic substrate.

Electrocardiographic alternans, a phenomenon of beat-to-beat alternation in cardiac electrical waveforms, has been implicated in the pathogenesis of ventricular arrhythmias and SCD. However, rather than merely being associated with an increased risk for SCD, several lines of pre-clinical and clinical evidence suggest that cardiac alternans may play a causative role in generating the electrophysiologic substrate necessary for the onset of ventricular arrhythmias.

The above-described systems and methods have shown that RA can be effectively estimated from body surface ECG signals, using smartphone. Also, the smartphone can provide a viable platform to process ECG signals in real-time and enable generation of alerts for the patient and the treating physician of an impending arrhythmia while the patient leads a normal day-to-day life. Further still, there is a strong connection between RA and the ischemic index, especially before a tachy-arrhythmic event, indicating the significance of RA in predicting a tachy-arrhythmic event at least in a similar patient population group.

Studies in normal hearts using optical mapping techniques have shown that discordant APD alternans (reflecting two adjacent areas of the myocardium that oscillate with opposite phase) is associated with a state of marked cardiac electrical instability, as evidenced by the fact that when ventricular fibrillation occurs following alternans, it only occurs after discordant APD alternans, but never concordant APD alternans. This unstable electrical substrate is consistently induced at a critical heart rate threshold and is largely independent of the pacing site, suggesting that it is caused by heterogeneities of cellular repolarization properties and not heterogeneous propagation delay.

Analysis of ambulatory body-surface electrograms (Holter monitors) from patients with coronary artery disease has demonstrated a sharp upsurge in RA magnitude (measured by time-domain techniques) within minutes prior to spontaneous VTE. RA amplitude reached a peak about 10 minutes prior to the onset of ventricular arrhythmia with a peak magnitude about 25% higher than during a mean baseline obtained 60 to 120 minutes prior the VTE. Sharp upsurges in T-wave alternans immediately preceding spontaneous ventricular arrhythmias have also been documented from body-surface ECGs (leads V1, V5 and aVF) in patients hospitalized for acute heart failure. In the above-described study using the systems and methods of the present disclosure, RA increased from a baseline of 18.6±2.1 µV to 27.9±4.6 µV (p <0.05) during the 15 to 30 mins prior to arrhythmia onset and remained elevated until the occurrence of VTE; results were similar across all 3 body surface leads.

Analysis of intra-cardiac EGMs from ICDs has demonstrated a sharp increase in RA magnitude immediately prior to spontaneous ventricular arrhythmias. However, a similar upsurge in RA has not been observed prior to induced ventricular arrhythmias or preceding inappropriate ICD shocks. A recent prospective, multi-center study has extended these observations by analyzing intra-cardiac EGMs from patients with ICDs. In this study, the magnitude of TWA/V prior to spontaneous VTE was significantly greater than during any of the four control data segments. Furthermore, in logistic regression models, each 10 µV increase in TWA/V was associated with an increase in odds of VTE of 2.2. These data show a close temporal association between surges in T-wave alternans/variability and onset of spontaneous ventricular arrhythmias.

Although the magnitude of surges in TWA measured from body-surface leads is less than that measured from intra-cardiac electrograms (EGMs), the aforementioned data shows that significant increases in T-wave alternans prior to the onset of spontaneous VTE can be measured from body-surface electrodes and may be used to predict acute arrhythmia susceptibility. Importantly, simultaneous measurement of RA from body-surface and intra-cardiac electrograms in the study using the systems and methods of the present disclosure and other studies has shown a high degree of correlation suggesting that these measurements are detecting the same electrical phenomenon.

Thus, the systems and methods of the present disclosure can be used to determine generate ischemic index and indicate or predict ischemic events. Furthermore, systems and methods are provided that can be performed using a mobile device, including a smartphone, to predict acute arrhythmia susceptibility, including spontaneous ventricular arrhythmias. The systems and methods provided herein can be used to provide alerts before a tachy-arrhythmic event.

Abnormal Respiratory Events

Figure 6:
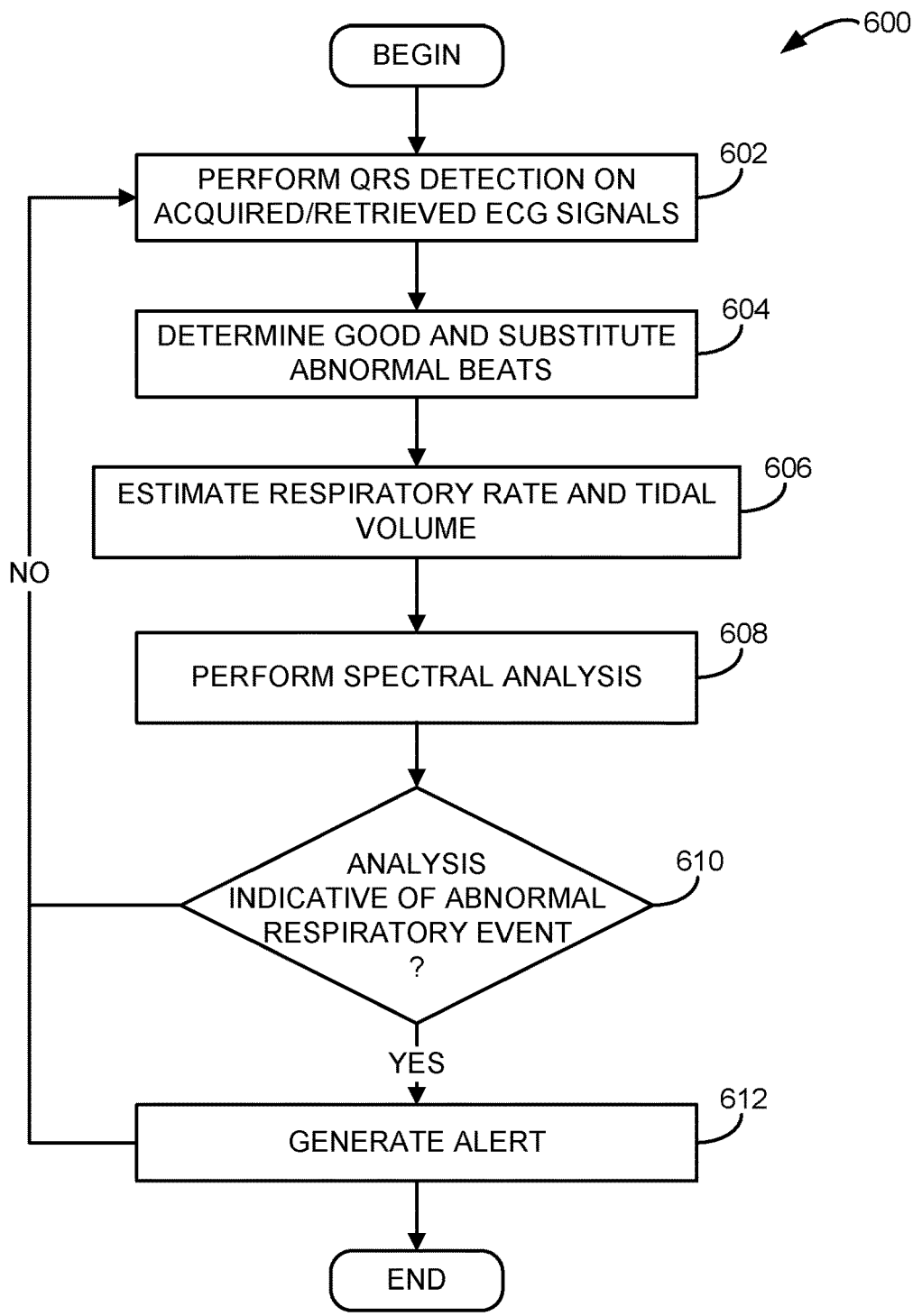
FIG. 6 is a flowchart setting forth steps of an exemplary process for determining abnormal respiratory events in accordance with the present disclosure.

As another non-limiting example, RR and/or TV can be used to detect abnormal respiratory events, including apnea events or apnea-related events or other abnormal respiratory patterns. One non-limiting example of an abnormal-respiratory detection process 600 is illustrated in FIG. 6. Specifically, the above-described QRS detection algorithm is performed at process block 602, which may include using the template-matching QRS alignment algorithm described above at process block 604. Then, at process block 606, RR and TV may be estimated, as described above with respect to FIG. 4.

At process block 608 a spectral analysis is performed to determine a rate corresponding to a frequency of the fast Fourier transform (FFT) spectrum indicative of an abnormal respiratory event. At decision block 610, the spectral spectrum is analyzed to determine if an abnormal respiratory event has occurred. In one non-limiting example, a rate corresponding to a frequency of the RR FFT spectrum that is below some value of cycles/beat can be considered to be an abnormal respiratory event. As a non-limiting example, a frequency of the RR FFT spectrum that is below 0.03 may be used as the threshold value indicative of an apnea event. That is, a 0.03 value of cycles/beat can be considered to be an apnea event. In another non-limiting example, a TV change beyond a selected threshold may indicate an apnea event. For example, TV change threshold of ~73 ml may be selected. Of course, these values may vary based on the individual, environmental conditions or the like. Thus, the system may be configured to learn or be optimized to the individual and even the individual over a given time period (e.g., during a night).

If, at decision block 610, an abnormal respiratory event is detected, an alert (visual, auditory, vibrational, or other alert) or report is generated at process block 612. In either case, the process iterates to continue monitoring for abnormal respiratory events.

Apnea-Related Studies

The above-described RR/TV-based estimation algorithms for diagnosing apnea were tested and showed to estimate the RR with an accuracy of 1 breath/min using only 2 ECG leads, ~91% of the time. Also, the RR/TV-based estimation algorithms for diagnosing apnea could estimate the TV with an accuracy of less than 105 ml using all 12 ECG leads, ~75% of the time. Further still, the RR/TV-based estimation algorithms for diagnosing apnea could detect apnea within ~7-8 seconds.

To determine the relationship of the number of ECG leads on the accuracy of the RR estimation, the RR was estimated by obtaining for each 32 beat sequence the ratio of any two body surface leads that provided an estimated error of less than 1 breath/min. In Table 1 the percent of RR estimations is provided across all animals that resulted in an error of less than 1 breath/min for the different pairs of leads.

TABLE 1

| Number of Pairs | Numerator & Denominator | Percent |
| --- | --- | --- |
| 1 | (V3, III) | 91.1 |
| 2 | (V3, III) (V2, V5) | 96.6 |
| 3 | (V3, III) (V2, V5) (V2, V1) | 98.3 |

Table 1 shows the pair of leads percent of RR estimations across all animals that resulted in error of less than 1 breath/min. Pairing of ECGIII with V3 was the most commonly selected coupling, accounting for 91% of all estimations, while paring V3 with III and V2 with V5 and V2 with V1, resulted in 98.3% of the RR estimates to exhibit an error less than 1 breadth/min.

To further evaluate this method in accurately estimating the TV from a minimum number of ECG leads, the TV was estimated by obtaining the lead(s) that exhibited a percent error smaller than the error limit (105 ml, median error) in at least one lead. We observe that, at least in swine, all 12 leads are required to achieve a TV estimate less than 105 ml, 75% of the time.

To assess the ability of the above-described smart-phone system to determine an apnea event, a study was performed where the ventilator was suspended for a period of ~0 sec between two normal breathing periods. The true RR values before and after apnea were 9 and 14 breaths/min respectively, while the estimated ones exhibited a less than one breath per min error. Assessing the time that the RR estimation algorithm needed to detect apnea (zero breaths per min), from normal breathing, we observed that, for an initial RR of 10.2±3.6 bpm (n=5), the above-described systems and methods were able to detect apnea at 7.9±1.1 sec.

While RR can be estimated at each heartbeat, TV estimation can be performed at each breathing cycle. During apnea, the estimated TV values reflect non-ventilation fluctuations of the RMS envelope, which are comparatively small (<100 ml) compared to TV of normal breathing. The real TV values before and after the apnea were 250 and 690 ml, respectively. In this particular example, the TV estimation errors before, during, and after apnea were 290 114.1±80.7 ml, 0±0 ml, and 150.5±168.1 ml, respectively. Overall, the error in TV estimation (n=5) before, during, and after apnea was −47.4±259.7 ml, 20.9±52.2 ml, and −86.1±177.4 ml, respectively. Again, seeking to assess the time need for TV estimation to detect apnea from normal breathing, we observed that for an initial TV 517.7±222.0 ml (n=5), the time needed to detect apnea was 5.5±2.2 sec.

In another non-limiting example, TV-based estimation of apnea error was evaluated. Linear regression between the estimated and true TV showed an R of 0.7877 (p<0.0001) at 6 breaths/min and 0.8233 (p<0.0001) at 14 breaths/min. This study determined that the TV estimation errors increase with incremental TV values, and the magnitude of these errors at 6 breaths/min is larger (p=0.61, 0.89 & 0.07 at 250, 500 & 750 ml, respectively, Wilcoxon rank sum test) than the errors at 14 breaths/min during non-apnea events.

In another non-limiting example, RR-based estimation of apnea showed that, among all estimated RR values, 97% exhibited errors of less than 1 breath/min. The TV and RR values estimated from 51 episodes of apnea were 11.7±54.9 ml and 0±3.5 breaths/min, which were significantly smaller than other non-apneic periods. During these apnea periods, the time the RR estimation algorithm needed to detect apnea was 7.0±3.2 s. When 73 ml was used as the threshold for apnea detection, the time the TV algorithm needed to detect apnea was 8.6±6.7 sec.

These results illustrated that the above-described TV/RR estimation algorithms can be applied for the detection of sleep apnea (SA), including Cheyne-Stokes respiration (CSR), whose breathing pattern is characterized by gradual increase and decrease of TV with periods of sleep apnea. The severity of sleep apnea is assessed by the apnea hypopnea index (AHI): the number of apneas and hypopneas per hour of sleep. The apnea/hypopnea in the index is defined as a cessation/reduction of breathing for 10 sec or more. The algorithms can be applied to estimate AHI from ECG signals.

Though the above-described systems and methods are described with selected thresholds, which may include predetermined or fixed thresholds, the above-described systems and methods may utilize dynamic thresholds or may include systems and methods that adapt the analysis process to the individual and/or medical conditions. For example, machine learning or artificial intelligence may be utilized to select thresholds or entirely replace the thresholds or process pipeline.

The present invention has been described in terms of one or more preferred embodiments, and it should be appreciated that many equivalents, alternatives, variations, and modifications, aside from those expressly stated, are possible and within the scope of the invention.

What is claimed is:

1. A mobile computing system comprising:
   a communication connection configured to communicate with an electrocardiographic (ECG) apparatus configured to acquire ECG signals from a subject through a plurality of ECG leads; and
   a processor configured to:
     receive the ECG signals through the communications connection;
     process the ECG signals to:
     estimate a respiratory rate of the subject by calculating SNR values for every possible combination of pairs of the ECG leads, selecting the pair of ECG leads with the highest SNR, and then estimating the respiratory rate by transforming the SNR values from the selected pair of ECG leads into the frequency domain and applying a Fourier Transform, wherein the respiratory rate is estimated from a predetermined sequence of beats based on the selected pair of leads, wherein a respiratory rate change threshold and a respiratory rate threshold are determined and an alert is generated when a change in the estimate of the respiratory rate is greater than the respiratory rate change threshold or the estimate of respiratory rate is greater than the respiratory rate threshold;
     estimate a tidal volume of the subject, estimating the tidal volume using one of: a percent modulation (PM) technique; a peak difference (PD) technique; or a combination of the PM technique and the PD technique, wherein a tidal volume change threshold and a tidal volume threshold are determined and an alert is generated when a change in the estimate of tidal volume is greater than the tidal volume change threshold or the estimate of tidal volume is greater than the tidal volume threshold;
     estimate an ischemic index of the subject and determine an ischemic index threshold, wherein an alert is generated when the estimate of ischemic index is greater than the ischemic index threshold; and
     estimate repolarization alternans of the subject, wherein the ischemic index and repolarization alternans are employed to predict an impending tachy-arrhythmic event, and an alert is generated when an impending tachy-arrhythmic event is predicted; and
   a display configured to display the alerts.

2. The system of claim 1 wherein the processor is further configured to determine at least one respiratory envelop from a respiration-induced, amplitude-modulated time-series of root-mean-squared (RMS) of the QRS complex from ECG signals acquired from the selected pair of ECG leads, on a beat-by-beat basis to estimate the respiration rate and the tidal volume.

3. The system of claim 2 wherein the processor is further configured to determine a set of power spectra using a fast Fourier transform (FFT) of the series of RMS amplitude ratios in a pre-defined beat number window, for the plurality of ECG lead combinations.

4. The system of claim 1 wherein the processor is further configured to compensate for premature ventricular contractions (PVCs) in estimating the respiration rate while controlling discontinuities in the RMS calculations based on the ECG signals by replacing aberrant beats with interpolated beats.

5. The system of claim 1 wherein the processor is further configured to determine a QRS complex from the ECG signals and determine whether the ischemic index is above a threshold value by calculating the ischemic index as an absolute value of a ratio of an amplitude of an ST segment to a QR amplitude in the QRS complex.

6. The system of claim 1 wherein the processor is further configured to analyze a Fourier spectrum of the respiratory rate and, upon determining a respiratory cycles per beat indicative of an abnormal respiratory event, generate an alert to indicate the abnormal respiratory event.

7. The mobile computing system of claim 1, wherein estimating tidal volume includes determining one of the ECG leads with a median PM value among all ECG leads and the tidal volume is estimated based on the ECG lead with the median PM value.

8. The mobile computing system of claim 1, wherein estimating tidal volume includes determining one of the ECG leads with a maximum PM value among all ECG leads and the tidal volume is estimated based on the ECG lead with the maximum PM value.

9. The mobile computing system of claim 1, wherein estimating tidal volume includes determining one of the ECG leads with a median PD value among all ECG leads and the tidal volume is estimated based on the ECG lead with the median PD value.

10. The mobile computing system of claim 1, wherein estimating tidal volume includes determining one of the ECG leads with a maximum PD value among all ECG leads and the tidal volume is estimated based on the ECG lead with the maximum PD value.

11. The mobile computing system of claim 1, wherein estimating tidal volume includes determining one of the ECG leads with a maximum PD value among all ECG leads, and the tidal volume is estimated based on a PM value of the ECG lead with the maximum PD value.

12. The mobile computing system of claim 1, wherein estimating tidal volume includes determining one of the ECG leads with a maximum PM value among all ECG leads, and the tidal volume is estimated using the PD value of that lead.

13. The mobile computing system of claim 1, wherein a mean baseline ischemic index value is determined for each ECG lead, and an alert is generated when the ischemic index at one of the ECG leads is above the mean baseline ischemic index value for said ECG lead.

14. The mobile computing system of claim 1, wherein an alert is generated when a repolarization alternans voltage is greater than 1 µV and a $K_{score}$ of the repolarization alternans voltage greater than 3.

15. The mobile computing system of claim 1, wherein the processor is further configured to: dynamically determine a tidal volume change threshold and a respiratory rate threshold based on the estimated respiratory rate and estimated tidal volume observed over time for a particular individual and their environmental conditions; and determine whether an abnormal respiratory event has occurred based on whether the tidal volume change threshold or the respiratory rate threshold has been exceeded.

* * * * *